(12) United States Patent
Kim et al.

(10) Patent No.: US 7,760,021 B2
(45) Date of Patent: Jul. 20, 2010

(54) VARIABLE GAIN AMPLIFIER

(75) Inventors: Chang Sun Kim, Gwangju-si (KR); Ki Jeon, Namyangju-si (KR)

(73) Assignee: Medison Co., Ltd., Kangwon-Do (KR)

( * ) Notice: Subject to any disclaimer, the term of this patent is extended or adjusted under 35 U.S.C. 154(b) by 90 days.

(21) Appl. No.: 12/326,830

(22) Filed: Dec. 2, 2008

(65) Prior Publication Data

US 2009/0140810 A1 Jun. 4, 2009

(30) Foreign Application Priority Data

Dec. 4, 2007 (KR) .................. 10-2007-0125066

(51) Int. Cl.
*H03F 3/45* (2006.01)
*H03G 3/10* (2006.01)
(52) U.S. Cl. ..................... 330/254; 330/284
(58) Field of Classification Search .............. 330/253, 330/254, 284

See application file for complete search history.

(56) References Cited

U.S. PATENT DOCUMENTS 5,684,431 A * 11/1997 Gilbert et al. ............... 330/254
6,812,771 B1 * 11/2004 Behel et al. ................. 330/254
7,362,178 B2 * 4/2008 Montemayor et al. ....... 330/284

FOREIGN PATENT DOCUMENTS

KR  2003-0079243  10/2003
KR  2006-0038250  5/2006

* cited by examiner

*Primary Examiner*—Khanh V Nguyen
(74) *Attorney, Agent, or Firm*—Jones Day

(57) ABSTRACT

The present invention relates to a variable gain amplifier. The variable gain amplifier in an ultrasound includes an attenuator. The attenuator includes resistor strings each having a plurality of resistors connected in series to each other and a gain control unit. The gain control unit has tap inputs taken from a plurality of junctions between a first resistor string receiving a first input signal and a second resistor string receiving a second input signal. The gain control unit is configured to provide an attenuated differential input signal based on the tap inputs. The variable gain amplifier includes an amplifying unit having a feedback amplifying section configured to amplify the attenuated differential input signal to output a first amplified signal and a clipping amplifying section configured to amplify the first amplified signal to output a second amplified signal that falls within a predetermined voltage range.

6 Claims, 7 Drawing Sheets

VARIABLE GAIN AMPLIFIER

The present application claims priority from Korean Patent Application No. 10-2007-0125066 filed on Dec. 4, 2007, the entire subject matter of which is incorporated herein by reference.

BACKGROUND OF THE INVENTION

1. Technical Field

The present invention generally relates to variable gain amplifiers, and more particularly to a variable gain amplifier with a wide gain range and a linear-in-dB characteristic for changing an external control voltage.

2. Background Art

An ultrasound diagnostic device has become an important and popular diagnostic tool due to its non-invasive and non-destructive nature. Modern high-performance ultrasound imaging diagnostic devices and techniques are commonly used to produce two- or three-dimensional images of internal features of patients.

The ultrasound diagnostic device generally uses a probe containing an array of piezoelectric elements to transmit and receive ultrasound signals. The ultrasound diagnostic device forms an image of human internal tissues by electrically exciting transducer elements to generate ultrasound signals that travel into the body. Echoes reflected from tissues and organs return to the transducer element and are converted into analog electrical receive signals (hereinafter referred to as "analog receive signals"). The transducer elements may output low amplitudes of the analog receive signals. Thus, the amplitudes of the analog electrical receive signals must be pre-amplified. The pre-amplification is carried out by a pre-amplifier installed on an output terminal of the transducer elements.

When the ultrasound signals are propagated into the tissues of the target object, their amplitudes are attenuated. Thus, the attenuation of the ultrasound signals has to be compensated to obtain an accurate ultrasound image. The compensation may be achieved by adjusting gain of the pre-amplified analog receive signals. The gain of the analog receive signals is usually adjusted by a variable gain amplifier.

The conventional variable gain amplifier may adjust the gain of the analog receive signals by using a passive element having a predetermined absolute value. In such a case, the absolute value of the element may vary according to an operation voltage or operation temperature. Thus, it may be difficult to accurately adjust the gain of the analog receive signals.

The compensated analog receive signals are inputted into an analog-to-digital converter (ADC) for digital processing. That is, the analog receive signals are converted into digital receive signals by the ADC. Subsequently, receive-focusing and digital signal processing are carried out upon the digital receive signals to thereby form ultrasound image data.

The analog receive signals may be amplified by the variable gain amplifier beyond an amplitude range allowable for input into the ADC. If the analog receive signals are amplified beyond an allowable amplitude range as an ADC input or a recovery time is increased due to overload, then the ADC may malfunction. As such, an accurate ultrasound image signal may not be obtained. Thus, a wide-band variable gain amplifier capable of outputting amplified analog receive signals within a limited amplitude range is needed.

DETAILED DESCRIPTION OF THE INVENTION

Figure 1:
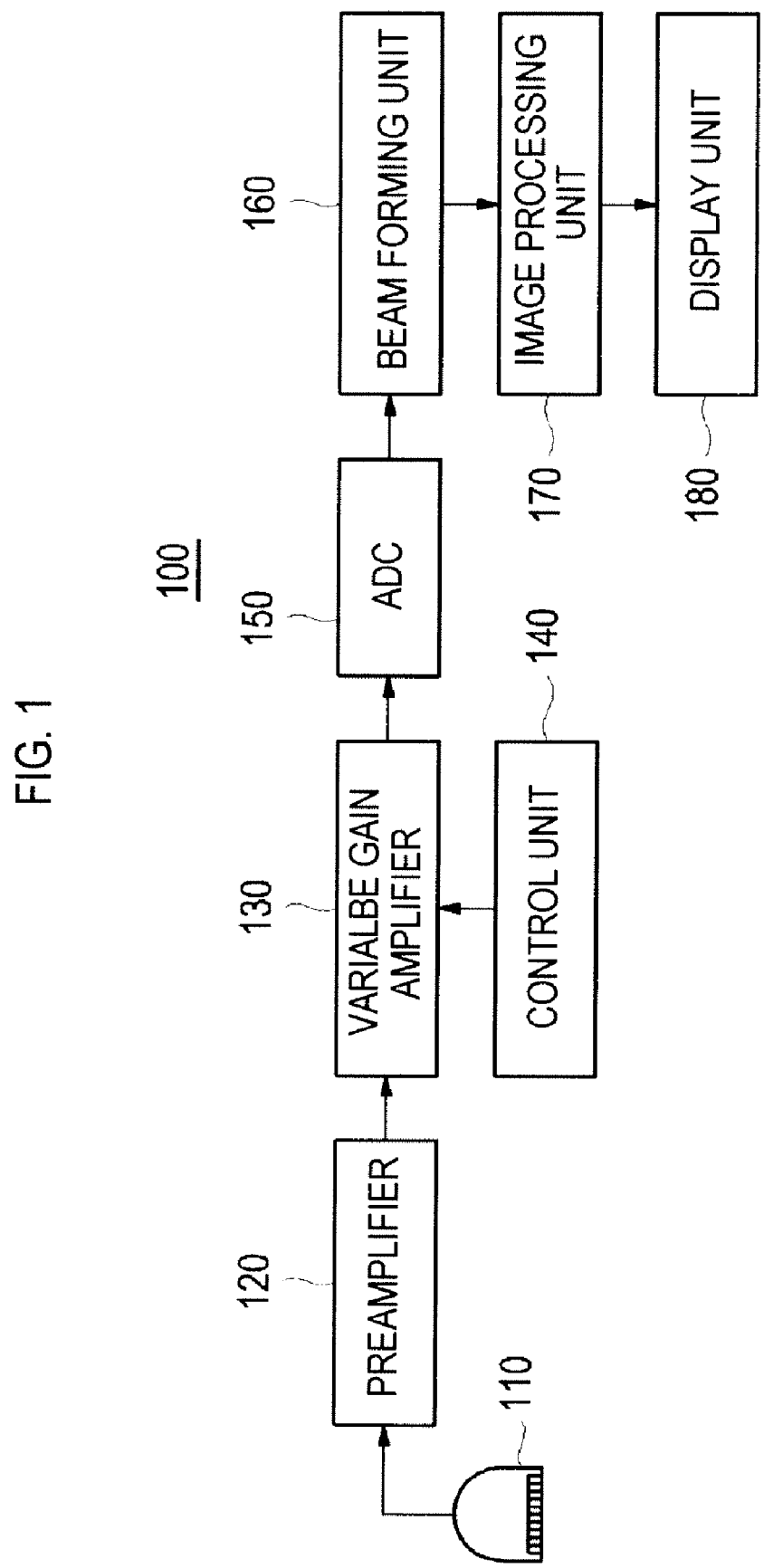
FIG. 1 is a block diagram showing an illustrative embodiment of an ultrasound diagnostic device.

FIG. 1 is a block diagram showing an illustrative embodiment of an ultrasound diagnostic device. As shown in FIG. 1, the ultrasound diagnostic 100 device may include a probe 110 containing at least one transducer element. The probe 110 may be configured to generate ultrasound signals in response to transmit pulse signals outputted from transmit pulsers (not shown) and transmit the ultrasound signals to a target object. Also, the probe 110 may receive ultrasound echoes reflected from the target object and convert the ultrasound echoes to analog receive signals, which are electrical signals. The ultrasound diagnostic 100 may include a preamplifier 120 for pre-amplifying the analog receive signals such that the analog receive signals have amplitudes capable of being processed in the ultrasound system 100.

The ultrasound diagnostic device may include a variable gain amplifier 130 for adjusting gains of the pre-amplified analog receive signals to compensate for attenuation of the ultrasound signals, which is caused during propagation in the target object. Amplitudes of analog receive signals corresponding to ultrasound echoes reflected at a near field from the probe 110 may be relatively strong, while amplitudes of analog receive signals corresponding to ultrasound echoes reflected at a far field from the probe 110 may be relatively weak. Thus, the variable gain amplifier 130 may be configured to relatively strongly attenuate the analog receive signals corresponding to the near field and to relatively weakly attenuate the analog receive signals corresponding to the near field. The variable gain amplifier 130 may be further configured to amplify the attenuation-compensated analog receive signals.

In one embodiment, the variable gain amplifier 130 may clip the analog receive signals to be within a predetermined voltage range, within which an analog-to-digital converter 150 of the next stage may normally function. The analog-to-digital converter 150 may convert the analog receive signals outputted from the variable gain amplifier 130 into digital signals.

The ultrasound diagnostic device 100 may include a control unit 140 for transmitting control signals to the variable gain amplifier 130 for variably controlling the gains of the analog receive signals depending on the depth. The ultrasound diagnostic device 100 may include a beam forming unit 160 for applying delays to the digital signals outputted from the analog-to-digital converter 150 and summing the delayed digital signals to thereby form receive focused beams. An image signal processing unit 170 may be configured to perform signal processing upon the receive focused beams in order to form image signals. A display unit 180 may receive the image signals to thereby display an ultrasound image of the target object.

Figure 2:
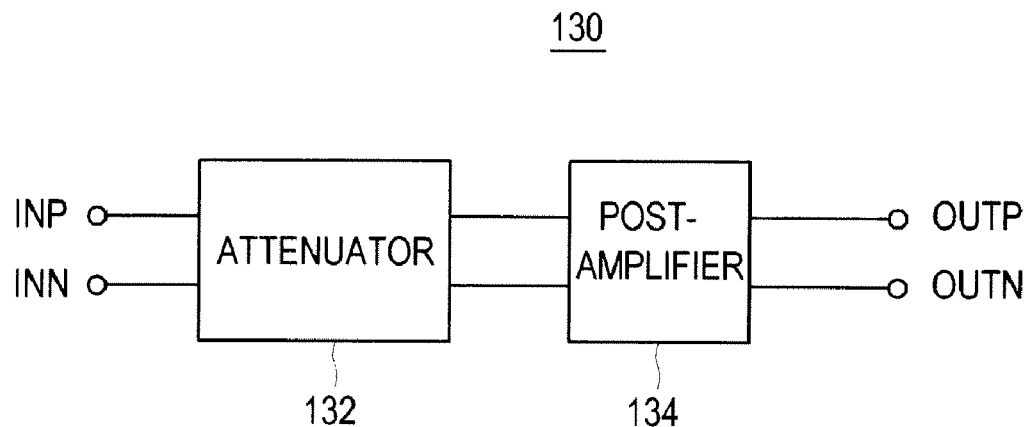
FIG. 2 is a block diagram showing an illustrative embodiment of a variable gain amplifier.

FIG. 2 is a block diagram showing an illustrative embodiment of the variable gain amplifier. As shown in FIG. 2, the variable gain amplifier 130 may include an attenuator 132 and a post amplifier 134.

The attenuator 132 may receive differential signals INP and INN outputted from the preamplifier 132 as input signals. The attenuator 132 may be configured to adjust gains of the differential signals INP and INN to compensate for the attenuation of the ultrasound signals with increasing depth. The attenuator 132 may be configured to increase gains of the differential signals corresponding to ultrasound echoes reflected from a near field of the probe 110 while decreasing gains of the differential signals corresponding to ultrasound echoes reflected from a near field of the probe 110. Thus, the attenuation of the ultrasound signals depending on the depth may be compensated. In one embodiment, the attenuator 132 may vary the gain of the differential signals INP and INN linearly.

Figure 3:
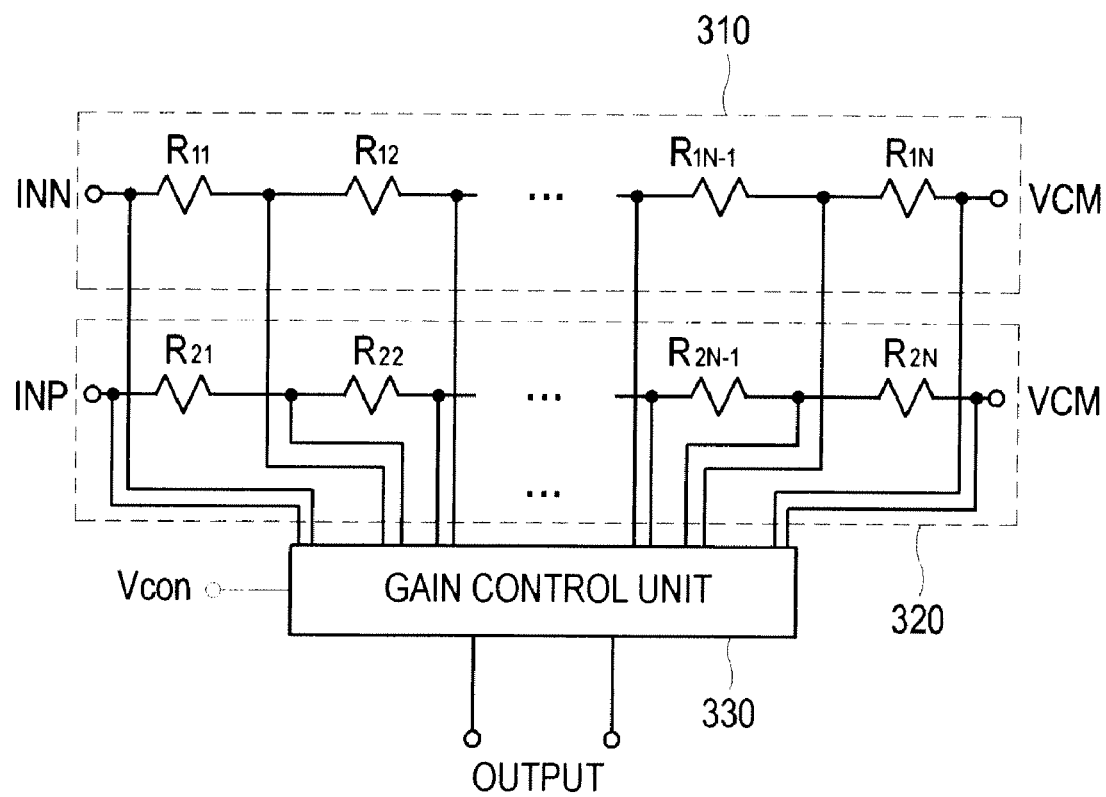
FIG. 3 is a circuit diagram showing an embodiment of an attenuator.

FIG. 3 is a circuit diagram showing an embodiment of the attenuator. As shown in FIG. 3, the attenuator 132 may include a first attenuation unit 310, a second attenuation unit 320 and a gain control unit 330. The first attenuation unit 310 may include a resistor string consisting of a plurality of resistors $R_{11}$-$R_{1N}$, which are connected to each other in serial, and a plurality of taps. The resistor string may receive a first input signal INN. In such a case, the taps may be set on junctions between the neighboring resistors. The second attenuation unit 320 may include a resistor string consisting of a plurality of resistors $R_{21}$-$R_{2N}$, which are connected in serial to each other, and a plurality of taps of the first attenuation unit 320. The resistor string of the second attenuation unit 320 may receive a second input signal INP. The taps may also be set on connection points between the neighboring resistors. The gain control unit 330 may be configured to output differential signals to variably have the gains in response to the control signals outputted from the control unit 120. In one embodiment, the resistor strings of the first and second attenuation units 310 and 320 may be commonly connected to a DC voltage VCM.

In one embodiment, the resistor strings of the first and second attenuation units 310 and 320 may be configured into an identical resistor string. The resistor string may be configured to have the same resistance ratio between the neighboring resistors. For example, the gain between the neighboring resistors in the resistor string may be set to 6 dB=20 log($R_{11}$/$R_{12}$)=20 log($R_{12}$/$R_{13}$)= . . . =20 log($R_{1N-1}$/$R_{1N}$) so that a linear-in-dB characteristic may be obtained. The resistance ratio may be set such that the gain becomes 2 dB or 3 dB to obtain a finer gain characteristic. Since the gain is adjusted by using the resistance ratio between the neighboring resistors in the resistor string in one embodiment, the gain may be stably adjusted for changes of element values, a power supply voltage and an operation temperature compared to the gain adjustment using elements having absolute values.

The gain control unit 330 may be configured to take tap inputs from one of the taps of the first and second attenuation units 310 and 320 in response to the control signals Vcon outputted from the control unit 120 to thereby output gain-controlled differential signals. In one embodiment, the gain control unit 330 may include a switching device capable of selecting one of the taps in the resistor string in response to the control signals.

Figure 4:
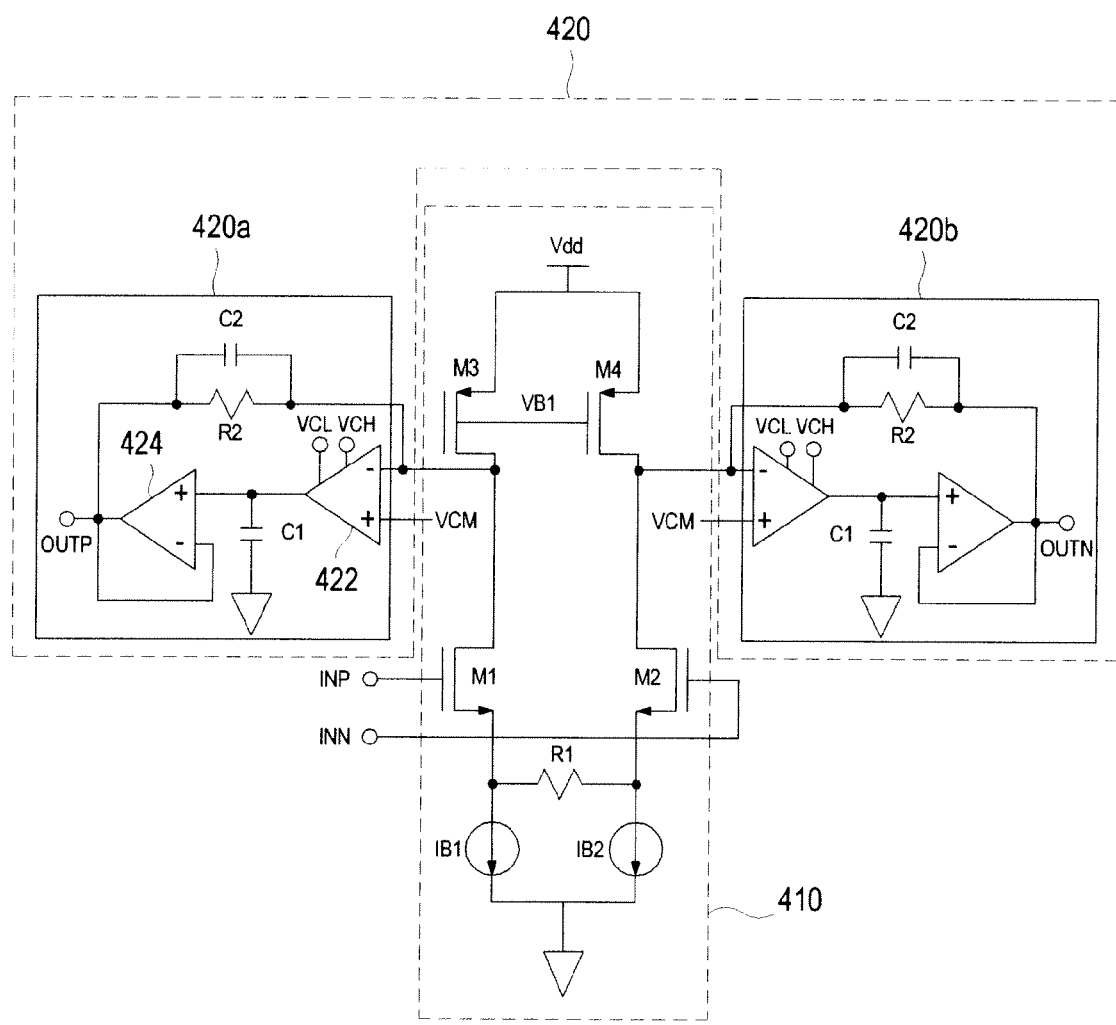
FIG. 4 is a detailed circuit diagram showing one embodiment of a post amplifier having a fixed gain.

FIG. 4 is a detailed circuit diagram showing one embodiment of the post amplifier with a gain fixed. The post amplifier 134 may include a first amplifying unit 410 and a second amplifying unit 420.

The first amplifying unit 410 may include first and second transistors M1 and M2, the gates of which receive the differential signals INP and INN outputted from the attenuator 132. It may also include a first resistor R1 coupled between sources of the first and second transistors M1 and M2. The first amplifying unit 410 may further include first and second current sources IB1 and IB2 each having one end coupled to a respective source of the first and second transistors M1 and M2 and the other end coupled to the ground. Also, the first amplifying unit 410 may further include transistors M3 and M4, which are coupled in parallel between the power supply voltage Vdd and drains of the first and second transistors M1 and M2. A bias voltage VB1 may be applied to gates of the transistors M3 and M4. This is so that a constant current may flow in the transistors M3 and M4 independent from variation of the power supply voltage Vdd.

The second amplifying unit 420 may include a first amplifying section 420a and a second amplifying section 420b. The first and second amplifying sections 420a and 420b may be configured to amplify signals outputted from drains of the first and second transistors of the first amplifying unit 410, respectively. By way of a non-limited example, the first amplifying section 420a may be identically configured with the second amplifying second 420b. For the sake of convenience, the configuration of the first amplifying section 420a will be described as an example.

The first amplifying section 420a may include a first operational amplifier (OP AMP) 422, a compensation capacitor C1 and a second OP AMP 424. The first amplifying section 420a may further include a second resistor R2 and a second capacitor C2, which are coupled between an input node of the first OP AMP 422 and an output node of the second OP AMP 421 in parallel. The first OP AMP 422 may receive a drain output of the first transistor M1 and a reference voltage VCM. Also, the first OP AMP 422 may receive clipping voltages VCL and VCH. The first OP AMP 422 may output signals, which are clipped at the clipping voltage VCL or VCH. The second OP AMP 424 may be configured to buffer the output signals of the first OP AMP 422. A unity-gain buffer may be used as the second OP AMP 424. The second OP AMP 424 may operate as a class AB OP in one embodiment so that a stand-by current may be reduced by 50%. Also, when an output voltage for the input signal of a 5 MHz sine wave is 1V (peak-to-peak), a second harmonic distortion and a third harmonic distortion may be 60 dBc and 64 dBc, respectively.

Figure 5:
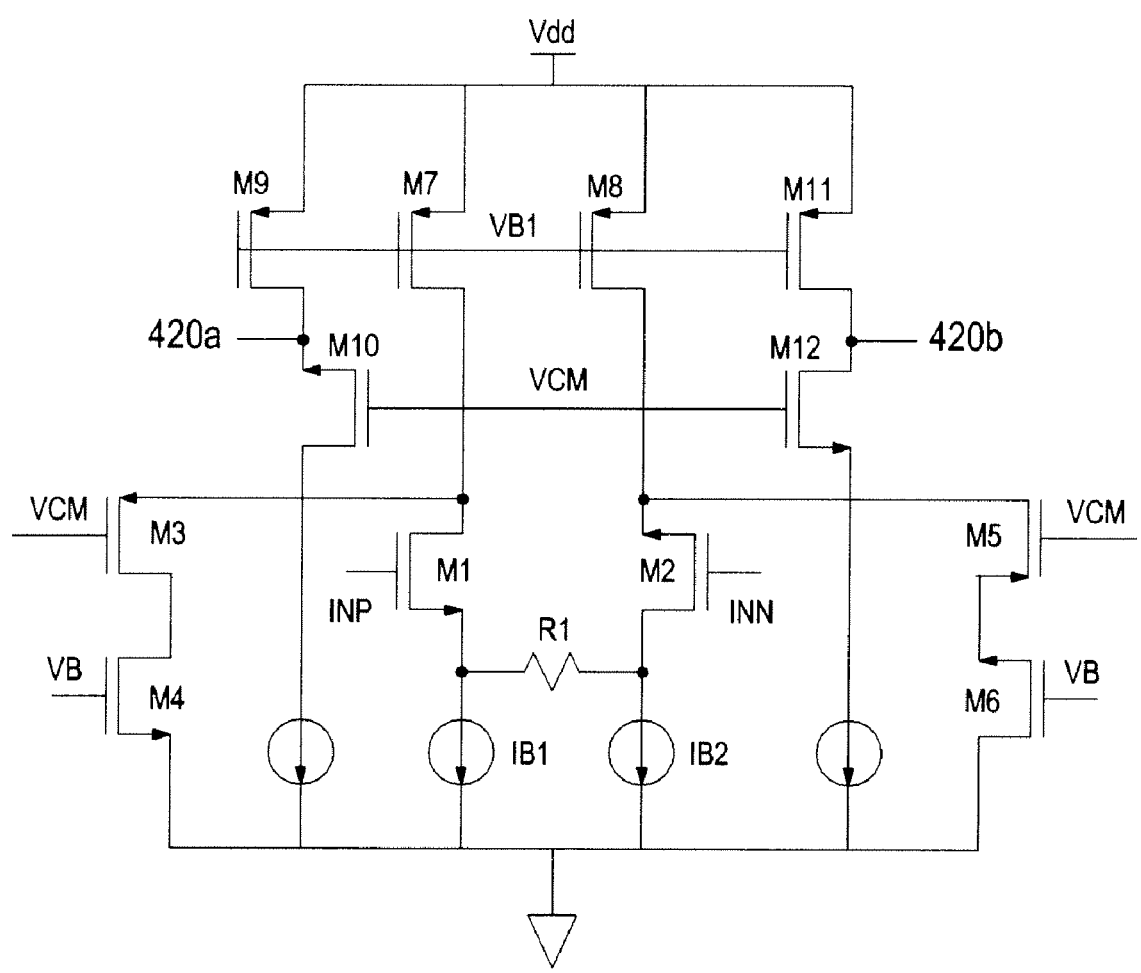
FIG. 5 is a detailed circuit diagram showing a first amplifying unit for increasing transconductance of input transistors in another embodiment of the present invention.

FIG. 5 is a detailed circuit diagram showing the first amplifying unit 410 for increasing transconductance of the input transistors in another embodiment of the present invention. As shown in FIG. 5, a feedback circuit consisting of transistors M1, M3 and M4 and a current source IB1 may be provided to increase the transconductance of the input transistor M1. An effective transconductance $gm_{eff}$ of the input transistor M1 receiving the differential signal INP may be defined by the following equation (1).

$$gm_{eff}=gm(1+fA) \quad (1)$$

wherein "f" represents a transconductance ratio of the transistors M1 and M3, and "A" represents a open loop gain that can be formed by removing feedback from the feedback loop.

In the same manner, a feedback circuit consisting of transistors M2, M5 and M6 and a current source IB2 may be provided to increase the transconductance of the input transistor M2 receiving the differential signal INN. The transconductance of the input transistors may be increased due to the feedback circuit. Thus, the first amplifying unit 410 may be insensitive against the changes of the operation voltage, element values or an operation temperature. The first amplifying unit 410 may further include transistors M7-M12, each coupled to the poser supply voltage Vdd and receiving bias voltages VB1 and VCM as their gate inputs for providing a constant current.

Figure 6:
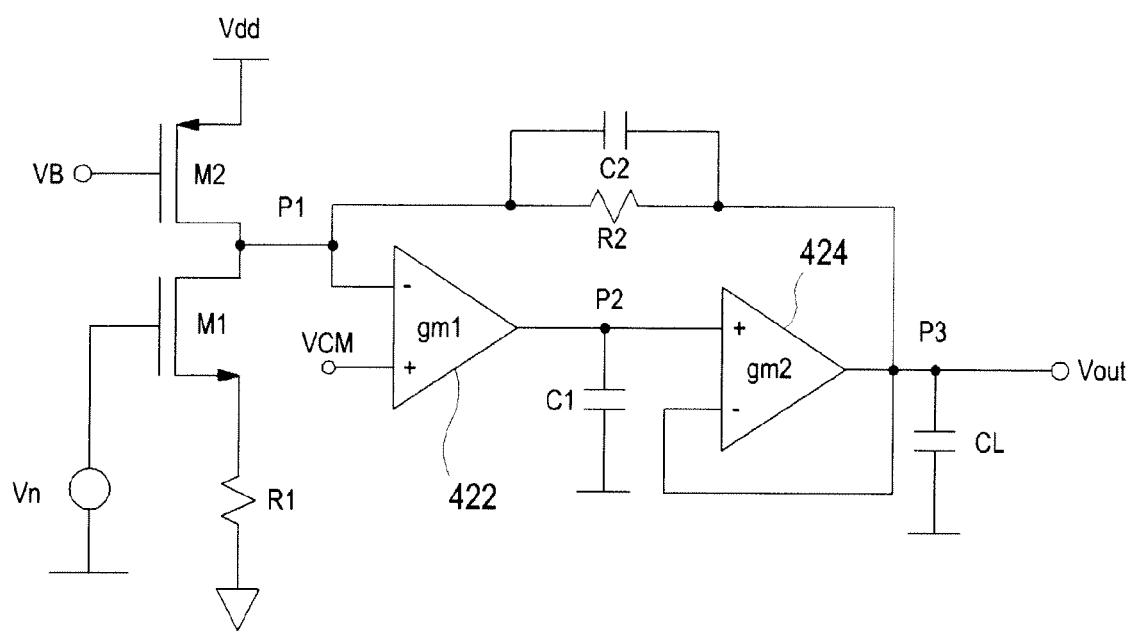
FIG. 6 is a circuit diagram showing an example of a small signal model for analyzing frequencies of the post amplifier in one embodiment.
Figure 7:
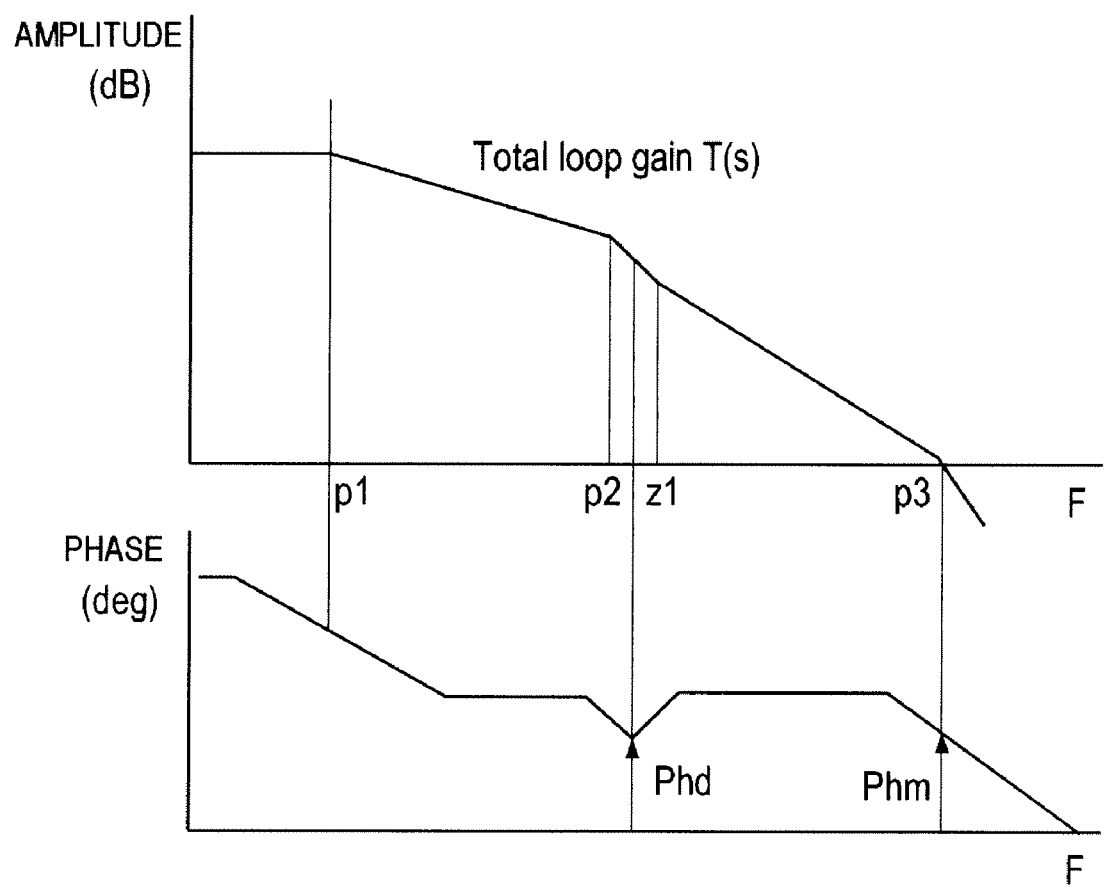
FIG. 7 is a bode plot showing amplitude and phase characteristics of the small signal model shown in FIG. 6.

FIG. 6 is a circuit diagram showing an example of a small signal model for analyzing frequencies of the post amplifier in one embodiment. Further, FIG. 7 shows a bode plot representing amplitude and phase characteristics at the small signal model shown in FIG. 6.

As shown in FIG. 6, the small signal model is configured with three stages P1-P3. A DC gain in the small signal model may be set by varying the value of R2/R1. As a resistor R2 and a miller capacitor C2 are coupled to each other in parallel, frequencies may be split into low frequencies at a first pole P1 and high frequencies at a second pole P2. Thus, a phase margin may be secured so that the frequencies may be compensated. Also, as a zero point is added by inserting a capacitor C1 at a second pole P2 or near thereof, the phase margin may be secured.

Figure 8:
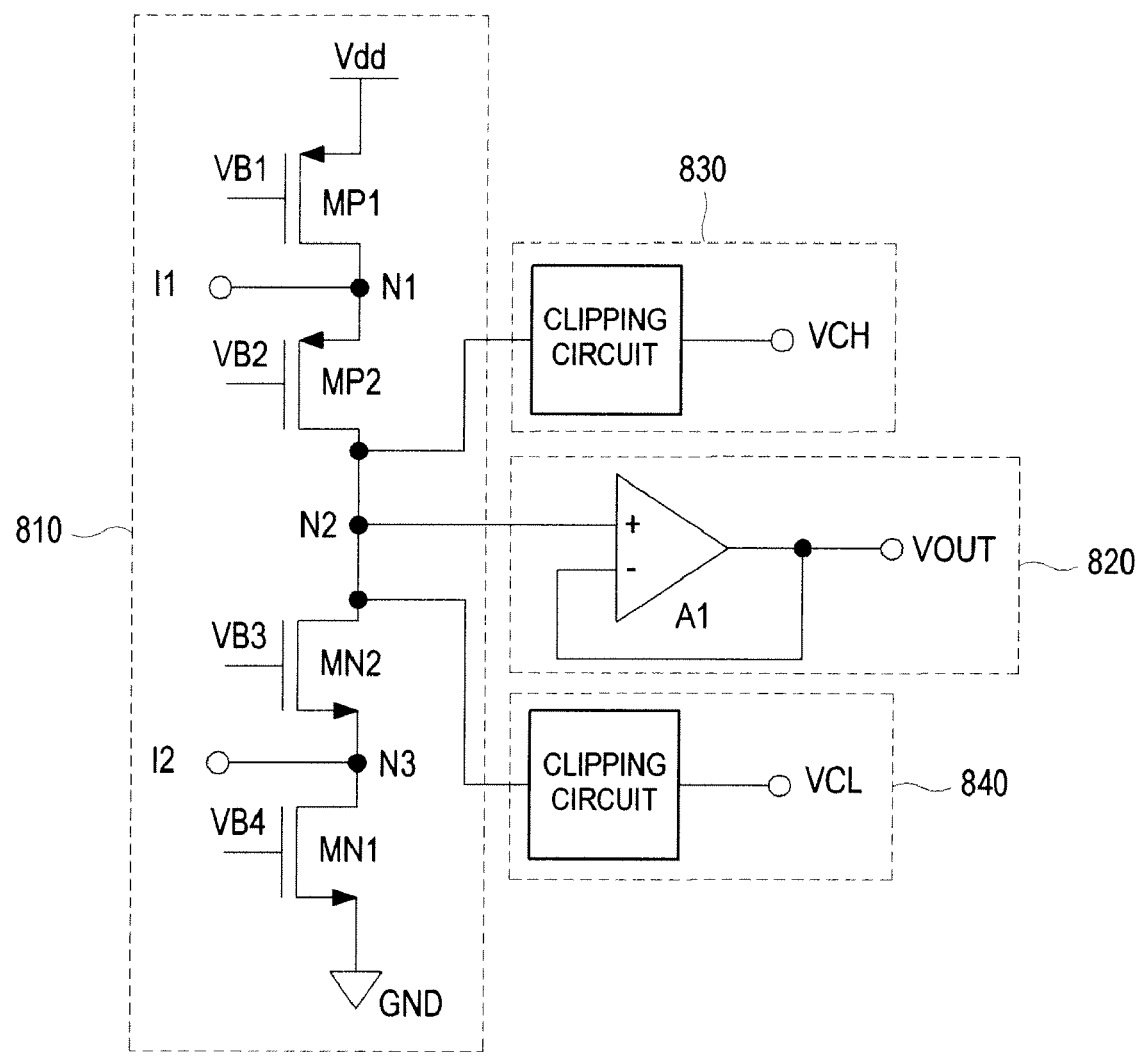
FIG. 8 is a circuit diagram showing the variable gain amplifier in accordance with one embodiment of the present invention.

FIG. 8 is a circuit diagram showing the variable gain amplifier 422 in one embodiment. As illustrated in FIG. 8, the variable gain amplifier 422 may include an input unit 810, an output unit 820, a first clipping unit 830 and a second clipping unit 840.

The input unit 810 may be configured to receive a first input signal I1 and a second input signal I2. The first and second input signals I1 and I2 are complementary in polarity. The input unit 810 may include a first node N1 for receiving the first input signal I1, a first P-type metal-oxide-semiconductor (PMOS) transistor MP1 coupled between a power supply voltage Vdd and the first node N1, and a second PMOS transistor MP2 coupled between the first node N1 and a second node N2. The first node N1 is the junction of the source and the drain of the PMOS transistors MP1 and MP2. The second node N2 is connected to the output unit 820. The input unit 810 may further include a third node N3 for receiving the second input signal I2, a first N-type metal-oxide-semiconductor (NMOS) transistor MN1 coupled between the third node N3 and a ground GND, and a second NMOS transistor MN2 coupled between the second node N2 and the third node N3. The third node N3 is the junction of the source and drain of the NMOS transistors MN1 and MN2. The second node N2 is a junction of the second PMOS transistor MP2 and the second NMOS transistor MN2.

Constant bias voltages VB1, VB2, VB3 and VB4 may be applied to the gates of the respective transistors MP1, MP2, MN1 and MN2. The current I flowing in a transistor may be defined as the following equation (2).

$$I = \frac{1}{2}\mu C_{ox}\frac{W}{L}(V_{gs} - V_{th})^2 \quad (2)$$

wherein μ represents mobility of majority carriers in the channel, W and L represent width and length of a gate, and Cox represents a capacitance of a gate oxide per unit area. As can be seen from equation (2), as for a known threshold voltage Vth of the transistor, the current I depends on a gate-source voltage Vgs. Since the power supply voltage Vdd is connected to the source of the first PMOS transistor MP1 and the constant bias voltage VB1 is applied to the gate thereof, a constant current $I_{MP1}$ flows in the first PMOS transistor MP1. Thus, a current $I_{MP2}$ flowing in the second POMS transistor MP2 may be defined as the following equation (3).

$$I_{MP2} = I_{MP1} - I1 \quad (3)$$

Since $I_{MP1}$ is a constant, $I_{MP2}$ depends on the first input signal I1. That is, if current of the first input signal I1 decreases, then $I_{MP2}$ increases so that a voltage level at the second node N2 increases.

Also, since the source of the first NMOS transistor MN1 is connected to the ground GND and the constant bias voltage VB3 is applied to a gate thereof, a constant current, $I_{MN1}$, may flow. Thus, a current $I_{MN2}$ flowing through the second NMOS transistor MN2 may be defined as the following equation (4).

$$I_{MN2} = I_{MN1} - I2 \quad (4)$$

Since $I_{MN1}$ is a constant, $I_{MN2}$ depends on the second input signal I2. That is, if a current of the first input signal I2 decreases, then $I_{MP2}$ increases so that the voltage level at the second node N2 increases.

The output unit 820 may include a first amplifier A1. The first amplifier A1 may be configured such that a first input terminal is connected to the second node N2 and an output thereof is fed back to a second input terminal.

The first clipping unit 830 may be configured to compare a voltage level of the second node N2 with a level of a first reference voltage VCH. The first reference voltage VCH may be determined by a maximum voltage capable of being processed by the ADC 150. If the voltage level of the second node N2 is greater than that of the first reference voltage VCH, then the first clipping unit 830 may be connected to the second node N2 such that the current of the second node N2 flows into the first clipping unit 830. Thus, an increase of the voltage level at the second node N2 over the level of the first reference voltage VCH can be prevented. That is, the voltage level of the second node N2 is clipped at the level of the first reference voltage VCH.

As mentioned above, the variable gain amplifier may determine the gain of the analog receive signals by using the resistor string consisting of the plurality of resistors in one embodiment. As such, the linear-in-dB variable gain amplifier may be implemented. Also, the gain of the attenuator is determined by a resistance ratio between the neighboring resistors. This is so that a constant gain may be obtained against the changes of the operation voltage, temperature or the like.

In accordance with one embodiment of the present invention, there is provided a variable gain amplifier in an ultrasound, comprising: an attenuator including resistor strings each consisting of a plurality of resistors connected in series to each other and a gain control unit, the gain control unit having tap inputs taken from a plurality of junctions between a first resistor string receiving a first input signal and a second resistor string receiving a second input signal, wherein the gain control unit is configured to provide an attenuated differential input signal based on the tap input; and an amplifying unit including a feedback amplifying section configured to amplify the attenuated differential input signal to output a first amplified signal and a clipping amplifying section configured to amplify the first amplified signal to output a second amplified signal that falls within a predetermined voltage range.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A variable gain amplifier for use in an ultrasound diagnostic device, comprising:
    an attenuator including resistor strings, each resistor string having a plurality of resistors connected in series to each other and to a gain control unit, the gain control unit having tap inputs taken from a plurality of junctions between a first resistor string receiving a first input signal and a second resistor string receiving a second input signal, wherein the gain control unit provides an attenuated differential input signal based on the tap inputs; and
    an amplifying unit including a feedback amplifying section configured to amplify the attenuated differential input signal to output a first amplified signal and a clipping amplifying section configured to amplify the first amplified signal to output a second amplified signal falling within a predetermined voltage range.

2. The variable gain amplifier of claim 1, wherein a resistance ratio of neighboring resistors in at least one of the first and second resistor strings is a constant value in dB.

3. The variable gain amplifier of claim 2, wherein the feedback amplifying section includes:
    first and second transistors for receiving the attenuated differential input signal outputted from the attenuator;
    third and fourth transistors coupled between the first and second transistors and a power supply voltage, respectively, wherein gates of the third and fourth transistors receive a bias voltage;
    fifth and sixth transistors coupled to the third and fourth transistors, wherein gates of the fifth and sixth transistors receive a bias voltage; and
    first and second current sources coupled to the first and second transistors.

4. The variable gain amplifier of claim 3, wherein the feedback amplifying section further includes:
    a first resistor coupled between a source of the first transistor and a source of the second transistor; and
    seventh and eighth transistors coupled between drains of the first and second transistors and a power supply voltage, wherein a bias voltage is applied to gates of the seventh and eighth transistors.

5. The variable gain amplifier of claim 4, wherein the clipping amplifying section includes:
    a first OP AMP receiving one of a drain output of the first and second transistors and a reference voltage and being configured to output a signal with a constant level clipped;
    a first compensation capacitor coupled to an output terminal of the first OP AMP;
    a second OP AMP receiving an output of the first OP AMP; and
    a second resistor and a second compensation capacitor coupled between an input terminal of the first OP AMP and an output terminal of the second OP AMP in parallel.

6. The variable gain amplifier of claim 5, wherein the second OP AMP includes a unity-gain buffer.

* * * * *

UNITED STATES PATENT AND TRADEMARK OFFICE
CERTIFICATE OF CORRECTION

PATENT NO. : 7,760,021 B2 Page 1 of 1
APPLICATION NO. : 12/326830
DATED : July 20, 2010
INVENTOR(S) : Kim et al.

It is certified that error appears in the above-identified patent and that said Letters Patent is hereby corrected as shown below:

On the title page, item 73, replace the assignee information to read:

-- Assignee: Medison Co., Ltd., Kangwon-do (KR);

Hivolic Co., Seoul (KR) --

Signed and Sealed this

Sixteenth Day of November, 2010

David J. Kappos
*Director of the United States Patent and Trademark Office*